United States Patent [19]
Bird et al.

[11] Patent Number: 5,304,490
[45] Date of Patent: Apr. 19, 1994

[54] DNA CONSTRUCTS CONTAINING FRUIT-RIPENING GENES

[75] Inventors: Colin R. Bird, Berkshire; Ruper G. Fray, Nottingham; Donald Grierson; Grantley W. Lycett, both of Loughborough; John A. Ray, Bracknell; Wolfgang W. Schuch, Crowthorne, all of England

[73] Assignee: Imperial Chemical Industries PLC, London, England

[21] Appl. No.: 748,761

[22] Filed: Aug. 23, 1991

[30] Foreign Application Priority Data

Aug. 24, 1990 [GB] United Kingdom ............... 9018612

[51] Int. Cl.$^5$ .................................... C12N 15/82
[52] U.S. Cl. ........................ 435/320.1; 435/172.3; 800/205; 800/DIG. 44; 536/23.6
[58] Field of Search .............. 435/320.1, 240.4, 172.3; 935/64, 67; 800/205, 250, DIG. 44, 64; 536/23.6

[56] References Cited

U.S. PATENT DOCUMENTS 5,034,323 7/1991 Jorgensen et al. ............... 435/172.3

OTHER PUBLICATIONS

Slater, et al. (1985) Plant Molecular Biology 5:137–147.
Napoli, et al. (Apr. 1990) The Plant Cell 3:279–289.
van der Krol, et al. (1990) Plant Molecular Biology 14:457–466.
van der Krol, et al. (Apr. 1990) The Plant Cell 2:291–299.
Tigchelaar, et al. (1989) in Griggs, et al., eds. *Tomato and pepper production in the tropics;* International Symposium on Integrated Management Practices, Taiwan, pp. 123–136.
Smith, et al. (1988) Nature 334:724–726.
Nagao, et al. (Dec. 1985) Molecular and Cellular Biology 5 (12):3417–3428.
Picton, et al. (1988) Plant, Cell and Environment 11:265–272.
Baumann et al, Functional analysis of sequences required for transcriptional activation of a soybean heat shock in transgenic tobacco plants, The EMBO Journal, vol. 6, No. 5, pp. 1161–1166, 1987.
Schuch et al, Control and manipulation of gene expression during tomato fruit ripening, Plant Molecular Biology, 13:303–311, 1989.
Hamilton et al, Antisense gene that inhibits synthesis of the hormone ethylene in transgenic plants, Nature, vol. 346, pp. 284–287, Jul. 19, 1990.
Schoffl et al, The DNA sequence analysis of soybean heat-shock genes and identification of possible regulatory promoter elements, The EMBO Journal, vol. 3, No. 11, pp. 2491–2497, 1984.

*Primary Examiner*—Che S. Chereskin
*Attorney, Agent, or Firm*—Cushman, Darby & Cushman

[57] ABSTRACT

DNA constructs useful for modifying the ripening behavior of fruit comprise a transcriptional initiation region operative in plants positioned for transcription of a DNA sequence homologous to some or all of a fruit-ripening gene encoded by either of the clones pTOM136 or pTOM66, so that the construct can generate RNA in plant cells. Also plant cells and plants transformed with such constructs.

3 Claims, 6 Drawing Sheets

FIG.1

SEQ ID NO: 1
SEQUENCE TYPE: Nucleotide
SEQUENCE LENGTH: 332 base pairs

STRANDEDNESS: single
TOPOLOGY: linear
MOLECULE TYPE: cDNA

ORIGINAL SOURCE ORGANISM: Tomato
IMMEDIATE EXPERIMENTAL SOURCE: Ripe tomato fruit cDNA library

FEATURES:

from 1 to 332 bp open reading frame

PROPERTIES: cDNA of tomato fruit ripening related gene - pTOM136

```
CTCCGGCAAC CTGAATCTCC TTTGAACCT TACCGCTAGC CTCCCCTCCTC CCATACCGGT    60
GCCACCTGAT TCGTTCTTCT CCCTCTTTCT CTCTGCTTCT CTCCCCGCTGA TCTGTAAAAT   120
CCTTCCTTCT TCTACTTCAA CTTTAACCTC CTCTTTCTTG AGCCCCGGAA CATCCATTTT   180
GAAGACGTGA GCTTGTGGGG TCTCTTTCCA ATCAATTTTT GCATTTGCAA AAGCAGAGAT   240
TTCACGAGAC AGAGGATGGG GTGTTGGCAA TTGGGAAGCC CTCGAAGGGA TCCCATAGGT   300
CAAGGGAAAA TGGGCCGAAG ATATTGCTTC AT                                 332
```

FIG.1 cont.

```
SEQ ID NO: 2
SEQUENCE TYPE: Nucleotide
SEQUENCE LENGTH: 652 base pairs

STRANDEDNESS: single
TOPOLOGY: linear
MOLECULE TYPE: cDNA

ORIGINAL SOURCE ORGANISM: Tomato
IMMEDIATE EXPERIMENTAL SOURCE: Ripe tomato fruit cDNA library

FEATURES:

from 45 to 509 bp openreading frame

PROPERTIES: cDNA of tomato fruit ripening related gene - pTOM66
```

| | | | | |
|---|---|---|---|---|
| TCAGCGCAAA | AAAACGTAGA | AAATTCTCAA | AAAGTTCACT | GAAAATGTCT | CTGATCCCAA | 60 |
| GAATTTTCGG | CGATCGACGA | AGCAGCAGCA | TGTTCGATCC | ATTTCAATT | GACGTATTTG | 120 |
| ATCCATTCAG | GGAATTAGGC | TTCCCAAGTA | CCAATTCAGG | GGAGAGCTCT | GCATTTGCCA | 180 |
| ACACACGAAT | AGACTGGAAG | GAAACTCCAG | AACCTCATGT | GTTCAAGGTT | GATCTTCCAG | 240 |
| GGCTTAAGAA | GGAGGAAGTC | AAAGTGGAAG | TCGAGGAGGA | TAGGGTTCTT | CAGATCAGCG | 300 |
| GAGAGAGGAA | CGTGGAGAAG | GAAGATAAGA | ATGATAAGTG | GCATCGCATG | GAGCGAAGCA | 360 |
| GCGGGAAATT | CATGAGGAGA | TTTAGACTTC | CGGAGAATGC | AAAGATGGAT | CAAGTTAAGG | 420 |
| CGTCTATGGA | GAATGGAGTG | CTTACTGTTA | CTGTTCCAAA | GGAAGAGGTG | AAGAAGCCTG | 480 |
| AGTCAAGTC | CATTGAGATC | TCTGGTTAAA | TGCTCTGGTT | GGGAACAAAC | CTGTAGTATT | 540 |
| AAGTCAAGTG | TGTACTGTCG | AAGATTTTGA | GTTTACTTAT | TTTCTGTCTG | TGTCTTGTGC | 600 |
| GCTGAGTCGT | TTTACTAGTT | GGTTGTTATC | TGTTTGATGT | ATTTTCCTTG | AG | 652 |

SEQUENCE LISTING ( 1 ) GENERAL INFORMATION:

( i i i ) NUMBER OF SEQUENCES: 2

(2) INFORMATION FOR SEQ ID NO:1:

(i) SEQUENCE CHARACTERISTICS:
     (A) LENGTH: 332 base pairs
     (B) TYPE: nucleic acid
     (C) STRANDEDNESS: single
     (D) TOPOLOGY: linear (ii) MOLECULE TYPE: cDNA (xi) SEQUENCE DESCRIPTION: SEQ ID NO:1:

| | | | | | | |
|---|---|---|---|---|---|---|
| CTCCGGCAAC | CTGAATCTCC | TTTTGAACCT | TACCGCTAGC | CTCCCTCCTC | CCATACCGGT | 60 |
| GCCACCTGAT | TCGTTCTTCT | CCCTCTTTCT | CTCTGCTTCT | CTCCCGCTGA | TCTGTAAAAT | 120 |
| CCTTCCTTCT | TCTACTTCAA | CTTTAACCTC | CTCTTTCTTG | AGCCCCGGAA | CATCCATTTT | 180 |
| GAAGACGTGA | GCTTGTGGGG | TCTCTTTCCA | ATCAATTTTT | GCATTTGCAA | AAGCAGAGAT | 240 |
| TTCACGAGAC | AGAGGATGGG | GTGTTGGCAA | TTGGGAAGCC | CTCGAAGGGA | TCCCATAGGT | 300 |
| CAAGGGAAAA | TGGGCCGAAG | ATATTGCTTC | AT | | | 332 |

(2) INFORMATION FOR SEQ ID NO:2:

(i) SEQUENCE CHARACTERISTICS:
     (A) LENGTH: 652 base pairs
     (B) TYPE: nucleic acid
     (C) STRANDEDNESS: single
     (D) TOPOLOGY: linear (ii) MOLECULE TYPE: cDNA (xi) SEQUENCE DESCRIPTION: SEQ ID NO:2:

| | | | | | | |
|---|---|---|---|---|---|---|
| TCAGCGCAAA | AAAACGTAGA | AAATTCTCAA | AAAGTTCACT | GAAAATGTCT | CTGATCCCAA | 60 |
| GAATTTTCGG | CGATCGACGA | AGCAGCAGCA | TGTTCGATCC | ATTTTCAATT | GACGTATTTG | 120 |
| ATCCATTCAG | GGAATTAGGC | TTCCCAAGTA | CCAATTCAGG | GGAGAGCTCT | GCATTTGCCA | 180 |
| ACACACGAAT | AGACTGGAAG | GAAACTCCAG | AACCTCATGT | GTTCAAGGTT | GATCTTCCAG | 240 |
| GGCTTAAGAA | GGAGGAAGTC | AAAGTGGAAG | TCGAGGAGGA | TAGGGTTCTT | CAGATCAGCG | 300 |
| GAGAGAGGAA | CGTGGAGAAG | GAAGATAAGA | ATGATAAGTG | GCATCGCATG | GAGCGAAGCA | 360 |
| GCGGGAAATT | CATGAGGAGA | TTTAGACTTC | CGGAGAATGC | AAAGATGGAT | CAAGTTAAGG | 420 |
| CGTCTATGGA | GAATGGAGTG | CTTACTGTTA | CTGTTCCAAA | GGAAGAGGTG | AAGAAGCCTG | 480 |
| AGGTCAAGTC | CATTGAGATC | TCTGGTTAAA | TGCTCTGGTT | GGGAACAAAC | CTGTAGTATT | 540 |
| AAGTCAAGTG | TGTACTGTCG | AAGATTTTGA | GTTTACTTAT | TTTCTGTCTG | TGTCTTGTGC | 600 |
| GCTGAGTCGT | TTTACTAGTT | GGTTGTTATC | TGTTTGATGT | ATTTTCCTTG | AG | 652 |

DNA CONSTRUCTS CONTAINING FRUIT-RIPENING GENES

This invention relates to DNA sequences of genes expressed during fruit ripening, DNA constructs containing these sequences, plant cells containing the constructs and plants derived therefrom. In particular it involves the use of antisense or sense RNA technology to control gene expression in plants.

As is well known, a cell manufactures protein by transcribing the DNA of the gene for that protein to produce messenger RNA (mRNA), which is then processed (eg by the removal of introns) and finally translated by ribosomes into protein. This process may be inhibited by the presence in the cell of "antisense RNA". By this term is meant an RNA sequence which is complementary to a sequence of bases in the MRNA in question: complementary in the sense that each base in the antisense sequence (read in the 3' to 5' sense) is capable of pairing with the corresponding base (G with C, A with U) in the MRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the MRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, in for example European Patent publication no 271988 to ICI (corresponding to U.S. Ser. No. 119,614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the amount of polygalacturonase and reduction in depolymerisation of pectins during tomato fruit ripening (Smith et al, Nature, 334, 724–726, 1988; Smith et al., Plant Molecular Biology, 13, 303–311, 1990). Thus antisense RNA has been proven to be useful in achieving downregulation of gene expression in plants.

The present invention is based in part on the isolation and characterisation of genes of hitherto unknown function. Genes from a family of related genes of unknown function have been cloned and characterised by DNA sequence analysis.

The genes in question are encoded (almost completely) in pTOM136 or pTOM66, the nucleotide sequences of which have not previously been determined.

According to the present invention we provide DNA constructs comprising a DNA sequence homologous to some or all of a fruit-ripening gene encoded by either of the clones pTOM136 or pTOM66, preceded by a transcriptional initiation region operative in plants, so that the construct can generate RNA in plant cells.

In a further aspect, the invention provides DNA constructs comprising a transcriptional initiation region operative in plants positioned for transcription of a DNA sequence encoding RNA complementary to a substantial run of bases showing substantial homology to a fruit-ripening gene encoded by pTOM136 or pTOM66. The invention also includes plant cells containing such constructs; plants derived therefrom showing modified ripening characteristics; and fruit and seeds of such plants.

The constructs of the invention may be inserted into plants to regulate the production of enzymes encoded by genes homologous to pTOM136 or pTOM66. Depending on the nature of the construct, the production of the enzymes may be increased, or reduced, either throughout or at particular stages in the life of the plant. Generally, as would be expected, production of the enzyme is enhanced only by constructs which express RNA homologous to the substantially complete endogenous pTOM136 or pTOM66 MRNA. What is more surprising is that constructs containing an incomplete DNA sequence substantially shorter than that corresponding to the complete gene generally inhibit the expression of the gene and production of the enzymes, whether they are arranged to express sense or antisense RNA.

The plants to which the present invention can be applied include commercially important fruit-bearing plants, in particular tomato. In this way, plants can be generated which have modified expression levels of pTOM66 or pTOM136 genes and which may have one or more of the following characteristics:

Novel flavour and aroma due to changes in the concentrations and ratios of the many aromatic compounds that contribute to the tomato flavour.

Sweeter tomatoes due to increased sugar accumulation, or to decrease in the accumulation of acids (e.g. citric or malic acid) thereby allowing the flavour of the sugars to dominate.

Modified colour due to inhibition of the pathways of pigment biosynthesis (e.g. lycopene, $\beta$-carotene).

Longer shelf life and better storage characteristics due to reduced activity of degradative pathways (e.g. cell wall hydrolysis).

Improved processing characteristics due to changed activity of enzymes contributing to factors such as: viscosity, solids, pH, elasticity.

Modified fruit shape thus improving packing and storage characteristics.

Extended leaf biosynthetic activity due to inhibition of enzymes responsible for the degradative processes involved in senescence (in particular, leaf senescence): thus improving plant productivity.

DNA constructs according to the invention preferably comprise a base sequence at least 10 bases in length for transcription into antisense RNA. There is no theoretical upper limit to the base sequence—it may be as long as the relevant MRNA produced by the cell—but for convenience it will generally be found suitable to use sequences between 100 and 1000 bases in length. The preparation of such constructs is described in more detail below.

The preferred DNA for use in the present invention is DNA derived from the clones pTOM136 or pTOM66. The required antisense DNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the cut DNA sequence is inverted with respect to its orientation in the strand from which it was cut.

In new vectors expressing antisense RNA, the strand that was formerly the template strand becomes the coding strand, and vice versa. The new vector will thus encode RNA in a base sequence which is complementary to the sequence of either pTOM136 or pTOM66 MRNA. Thus the two RNA strands are complementary not only in their base sequence but also in their orientations (5' to 3').

Figure 1:
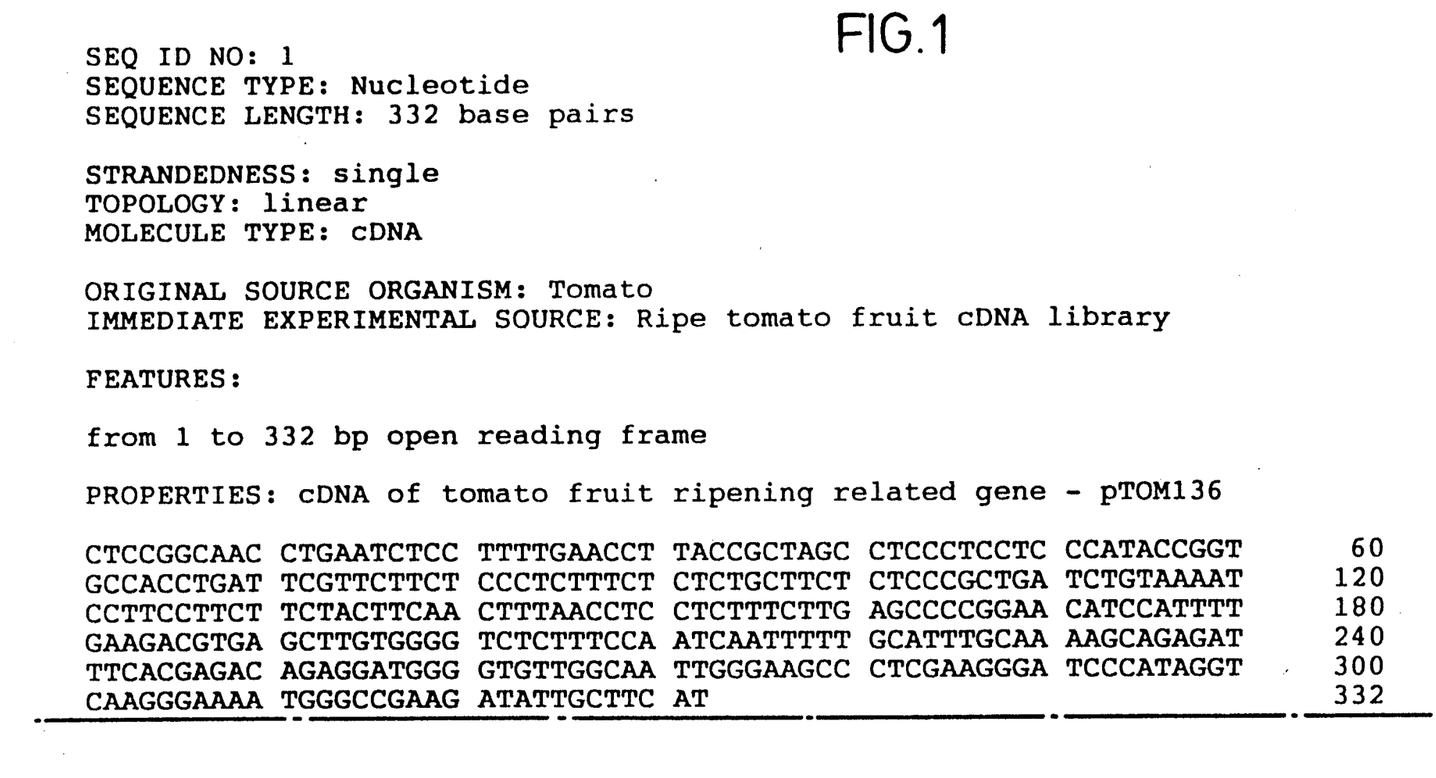
FIG. 1 shows the base sequence of the clones pTOM136 (SEQ ID NO: 1) and pTOM66 (SEQ ID NO: 2)

The base sequences of pTOM136 and pTOM66 are set out in FIG. 1. Searches in DNA and protein data bases have revealed homology to known genes from soybean, wheat, chenopodium and Arabidopsis which have enhanced expression revels after heat stress (Schoffl et al, EMBO Journal, 3, 2491-2497, 1984; McElwain and Spiker, Nucleic Acids Research, 17, 1764, 1989; Knack and Kloppstech, Nucleic Acids Research, 17, 5380, 1989;Helm and Vierling, Nucleic Acids Research, 17, 7995, 1989).

pTOM136 and pTOM66 have been deposited on 14 Jun. 1990 with the National Collections of Industrial and Marine Bacteria, Aberdeen, under Accession Nos. NCIB 40293 and NCIB 40292, respectively. pTOM136 and pTOM66 were originally derived from a CDNA library isolated from ripe tomato RNA (Slater et al Plant Molecular Biology 5, 137-147, 1985). If desired, suitable CDNA for use in the present invention may be obtained by repeating the work of Slater et al. In this way may be obtained sequences coding for the whole, or substantially the whole, of the mRNAs produced by either pTOM136 or pTOM66. Suitable lengths of the CDNA so obtained may be cut out for use by means of restriction enzymes.

Two other clones (pTOM125 and pTOM128) from Slater's cDNA library cross-hybridise to pTOM136 and probably contain related sequences. DNA sequence analysis has demonstrated that the CDNA inserts of pTOM136 and pTOM66 are 393 and 652 bases long respectively.

It has been shown that the mRNAs for which pTOM136 and pTOM66 code are expressed in ripening tomato fruit. No expression of pTOM66 could be detected in green fruit (Picton, PhD thesis University of Nottingham, 1989). However pTOM136 expression was detected in green fruit (Knapp, PhD thesis, University of Nottingham, 1988). pTOM136 and pTOM66 are expressed most strongly at the full orange stage of ripening. The levels of MRNA then decline in line with the general decline in biosynthetic capacity of the ripening fruit. The expression of pTOM136 is reduced in the known Ripening inhibitor (rin) and Neverripe (Nr) tomato fruit ripening mutants which mature very slowly.

The expression of a gene substantially homologous to the pTOM66 gene is transiently enhanced by incubation of ripening tomato fruit at 35° C. (Picton S. and Grierson D. Plant Cell Environ. 11, 265-272, 1988). If incubation at this temperature is continued, pTOM66-related MRNA does not accumulate to the same level as in fruit incubated at 250C. The transient expression of the pTOM66 related gene in response to heat stress is typical of the heat shock response that has been observed in nearly all organisms and tissues studied (Schlesinger et al, "Heat Shock from Bacteria to Man"; Cold Spring Harbour Laboratory, New York, 1982). It is not known whether the expression of the genes encoding pTOM136 and other related cDNAs is enhanced by heat stress. An MRNA highly homologous to pTOM66 has also been shown to accumulate during tomato leaf senescence (Davies and Grierson, Planta, 179, 73-80, 1989).

Although a considerable body of information on the structure and expression of the pTOM136 and pTOM66 gene family is known, the biochemical function of the products of these genes has not hitherto been fully elucidated. It is unlikely that the response to heat stress is the primary function of these genes.

An alternative source of DNA for the base sequence for transcription is a suitable gene encoding the pTOM136 or pTOM66 proteins. This gene may differ from the CDNA of, e.g. pTOM136 or pTOM66 in that introns may be present. The introns are not transcribed into MRNA (or, if so transcribed, are subsequently cut out). when using such a gene as the source of the base sequence for transcription it is possible to use either intron or exon regions. A further way of obtaining a suitable DNA base sequence for transcription is to synthesise it ab initio from the appropriate bases, for example using FIG. 1 as a guide.

Recombinant DNA and vectors according to the present invention may be made as follows. A suitable vector containing the desired base sequence for transcription (for example pTOM136 or pTOM66) is treated with restriction enzymes to cut the sequence out. The DNA strand so obtained is cloned (if desired, in reverse orientation) into a second vector containing the desired promoter sequence (for example cauliflower mosaic virus 35S RNA promoter or the tomato polygalacturonase gene promoter sequence—Bird et al., Plant Molecular Biology, 11, 651-662, 1988) and the desired terminator sequence (for example the 3' of the *Agrobacterium tumefaciens* nopaline synthase gene, the nos 3' end).

According to the invention we propose to use both constitutive promoters (such as cauliflower mosaic virus Ca MV 35S) and inducible or developmentally regulated promoters (such as the ripe-fruit-specific polygalacturonase promoter) as circumstances require. Use of a constitutive promoter will tend to affect functions in all parts of the plant: while by using a tissue-specific promoter, functions may be controlled more selectively. Thus in applying the invention, e.g. to tomatoes, it may be found convenient to use the promoter of the PG gene (Bid et al, 1988, cited above). Use of this promoter, at least in tomatoes, has the advantage that the production of antisense RNA is under the control of a ripening-specific promoter. Thus the antisense RNA is only produced in the organ in which its action is required. Among other ripening-specific promoters that could be used is the EB promoter (Deikman & Fischer, EMBO Journal 7, 3315-3320, 1988).

Vectors according to the invention may be used to transform plants as desired, to make plants according to the invention. Dicotyledonous plants, such as tomato and melon, may be transformed by Agrobacterium Ti plasmid technology, for example as described by Bevan (1984) Nucleic Acid Research, 12, 8711-8721. such transformed plants may be reproduced sexually, or by cell or tissue culture.

The degree of production of antisense RNA in the plant cells can be controlled by suitable choice of promoter sequences, or by selecting the number of copies, or the site of integration, of the DNA sequences according to the invention that are introduced into the plant genome.

In this way it may be possible to modify ripening or senescence to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, as well as tomatoes, fruits such as mangoes, peaches, apples, pears, strawberries, bananas and melons.

The invention will now be described further with reference to the accompanying drawings, in which.

The following Examples illustrate aspects of the invention.

EXAMPLE 1

Identification of the base sequences of pTOM136 and pTOM66

The base sequences of pTOM136 and pTOM66 have not previously been determined. The sequences were determined by standard DNA sequencing procedures and are shown in FIG. 1. Knowledge of these sequences is essential for determining the orientation of the open reading frame and the subsequent construction of RNA antisense vectors.

EXAMPLE 2

Construction of pTOM136 antisense RNA vectors with the CaMV 35S promoter

Figure 2:
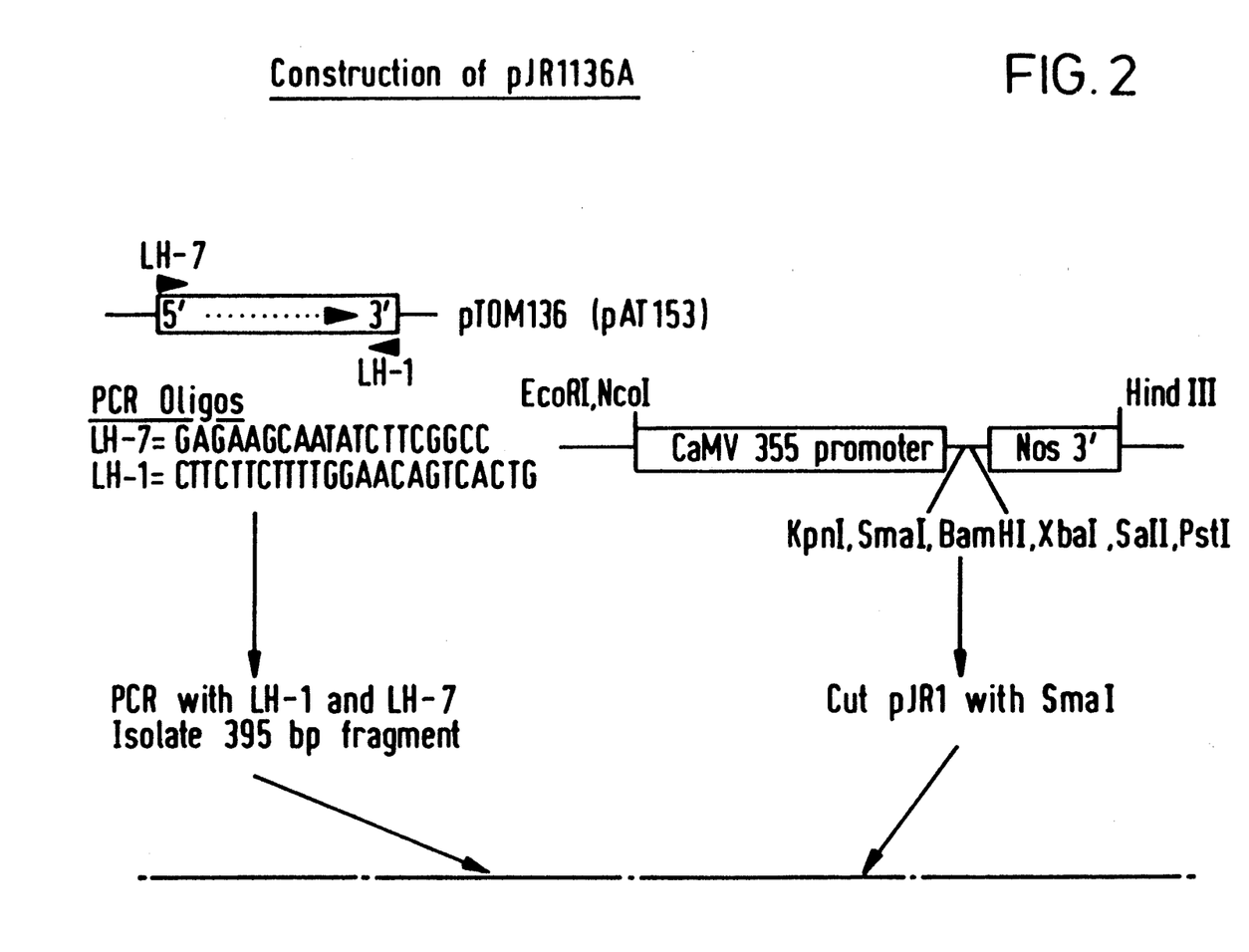
FIG. 2 shows the method of construction of pJR1136A.

The vector pJR1136A was constructed using the sequences corresponding to bases 1 to 393 of pTOM136 (FIG. 2). This fragment was synthesised by polymerase chain reaction using synthetic primers. The fragment was cloned into the vector pJR1 which had previously been cut with SmaI. pJR1 (Smith et al Nature 334, 724–726, 1988) is a Bin19-based vector (Bevan, Nucleic Acids Research, 12, 8711–8721, 1984), which permits the expression of the antisense RNA under the control of the CaMV 35S promoter. This vector includes a nopaline synthase (nos) 3' end termination sequence.

After synthesis of the vector, the structure and orientation of the pTOM136 sequence were confirmed by DNA sequence analysis.

EXAMPLE 3

Construction of pTOM66 antisense RNA vectors with the CaMV 35S promoter

Figure 3:
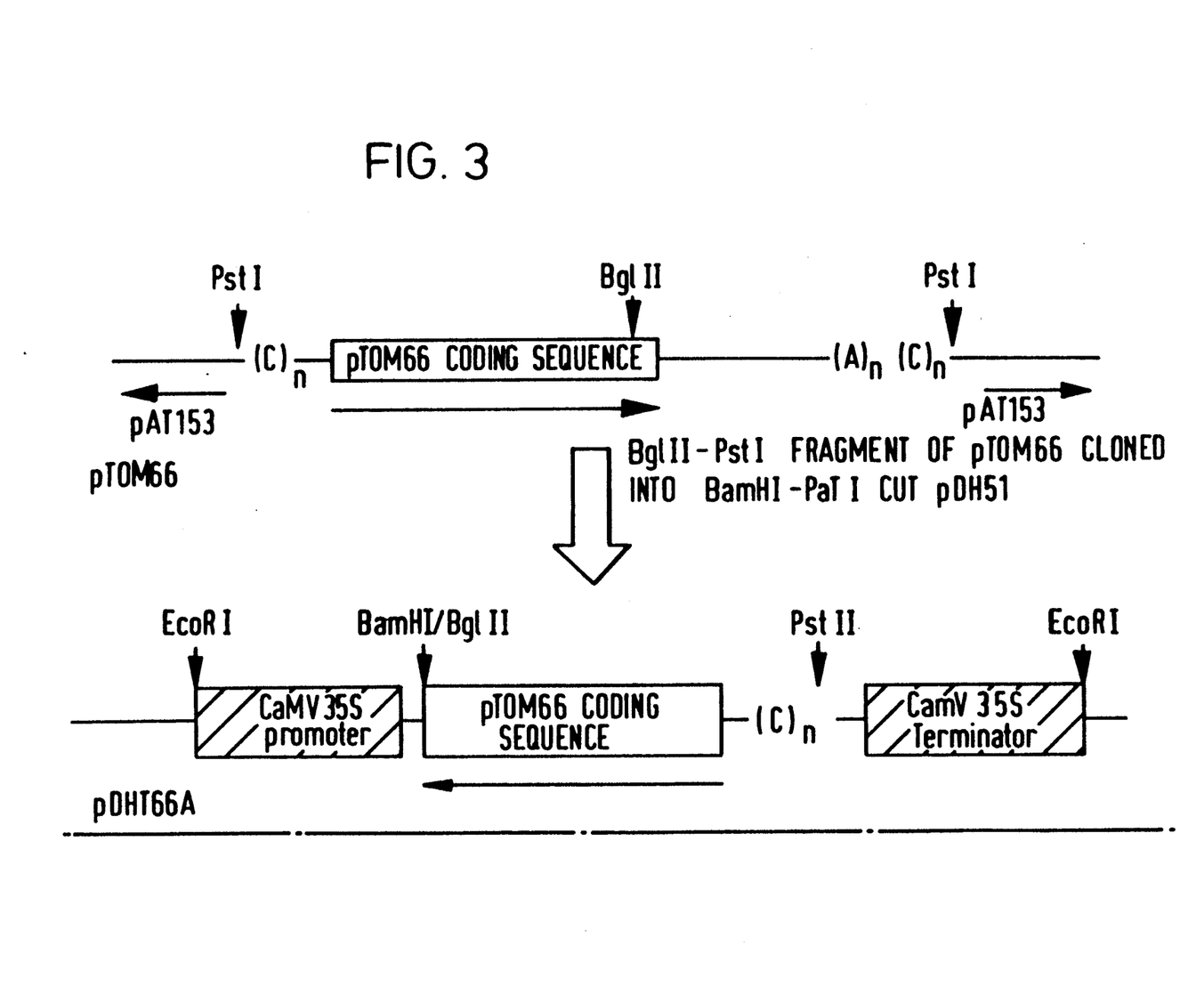
FIG. 3 shows the method of construction of pBDHT66A.

The vector pBDHT66A was constructed using the sequence corresponding to bases 1 to 500 of pTOM66 (FIG. 3).

This fragment was isolated from pTOM66 by restriction with BglII and PstI. It was then cloned into the vector pDH51 (Pietrzak et al, Nucleic Acids Research 14, 5857–5868) which had previously been cut with BamHI and PstI. An EcoR1 fragment was then transferred to Bin 19 cut with EcoR1.

After synthesis of the vector, the structure and orientation of the pTOM66 sequence were confirmed by DNA sequence analysis.

EXAMPLE 4

Construction of pTOM136 and pTOM66 antisense RNA vectors with the polygalacturonase promoter The fragments of the pTOM136 and pTOM66 cDNAs that were described in examples 2 and 3 are also cloned into the vector pJR2 to give pJR2136A and pJR266A respectively. pJR2 is a Bin19-based vector, which permits the expression of the antisense RNA under the control of the tomato polygalacturonase promoter. This vector includes a nopaline synthase (nos) 3' end termination sequence. After synthesis, vectors with the correct orientation of pTOM136 or pTOM66 sequences are identified by DNA sequence analysis.

EXAMPLE 5

Construction of pTOM136 and pTOM66 sense RNA vectors with the CaMV 35S promoter

The fragments of pTOM136 and pTOM66 cDNAs described in examples 2 and 3 are cloned into the vectors pJR1 and pDH51 in the sense orientation to give pJR1136S, pJR166S, pDH1136S and pDH166S, respectively.

After synthesis, the vectors with the sense orientation of pTOM136 or pTOM66 sequence are identified by DNA sequence analysis.

EXAMPLE 6

Production and analysis of transformed plants

Vectors were transferred to *Agrobacterium tumefaciens* LBA4404 (a micro-organism widely available to plant biotechnologists) and were used to transform tomato plants. Transformation of tomato stem segments follow standard protocols (e.g. Bird et al Plant Molecular Biology 11, 651–662, 1988). Transformed plants were identified by their ability to grow on media containing the antibiotic kanamycin. Plants were regenerated and planted to be grown to maturity. Ripening fruit of such plants will be analysed for modifications to their ripening characteristics.

---

We claim:

1. DNA constructs comprising a DNA sequence capable of encoding a fruit-ripening gene and contained in either of the clones pTOM136 or pTOM66, preceded by a transcriptional initiation region operative in plants, so that the construct can generate RNA in plant cells.

2. A DNA construct as claimed in claim 1 wherein the construct generates RNA complementary to RNA generated from a fruit-ripening gene encoded by either of the clones pTOM136 or pTOM66.

3. A DNA construct as claimed in claims 1 or 2 in which the DNA sequence derives from DNA.

* * * * *